US006221391B1

(12) United States Patent
Rouffer

(10) Patent No.: US 6,221,391 B1
(45) Date of Patent: *Apr. 24, 2001

(54) SELF-EMULSIFYING IBUPROFEN SOLUTION AND SOFT GELATIN CAPSULE FOR USE THEREWITH

(75) Inventor: Mark T. Rouffer, Windsor (CA)

(73) Assignee: Accucaps Industries Limited (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/197,616

(22) Filed: Nov. 23, 1998

(51) Int. Cl.[7] .............................. A61K 9/64; A61K 9/48; A61K 9/66; A61K 31/19; A01N 37/10
(52) U.S. Cl. ......................... 424/456; 424/452; 424/455; 514/570
(58) Field of Search ................................... 424/450, 451, 424/452, 453, 455, 456; 514/570

(56) References Cited

U.S. PATENT DOCUMENTS

| 4,690,823 | * | 9/1987 | Lohner et al. ................. 424/456 |
| 4,917,885 | * | 4/1990 | Chiba et al. ................... 424/78 |
| 5,071,643 | * | 12/1991 | Yu et al. ...................... 514/570 |
| 5,318,960 | * | 6/1994 | Toppo ......................... 514/159 |
| 5,626,872 | * | 5/1997 | Vasquez ....................... 424/451 |
| 5,641,512 |   | 6/1997 | Cimiluca ...................... 424/455 |

FOREIGN PATENT DOCUMENTS

| 44 12 201 A1 | 11/1994 | (DE) | ............................. A61K/37/02 |
| 0 254 693 A1 | 1/1988 | (EP) | ............................. A61K/31/40 |
| 0 274 870 | * | 7/1988 | (EP) . |
| 0 274 870 A2 | 7/1988 | (EP) | ............................. A61K/9/10 |
| 715879 | 9/1954 | (GB) | ............................. B11B/2/81 |
| 88/02625 | 4/1988 | (WO) | ............................ A61K/9/66 |

OTHER PUBLICATIONS

Book entitled "Polyoxyethylene Castor Oil Derivatives," pp. 371–373.
Product Information Sheets—Soluble Kollidon (Jun. 1993) "Soluble polyvinylpyrrolidone (polyvidone, povidone) for the pharmaceutical industry".

\* cited by examiner

*Primary Examiner*—Gollamudi S. Kishore
*Assistant Examiner*—Todd D. Ware
(74) *Attorney, Agent, or Firm*—Gifford, Krass, Groh, Sprinkle, Anderson & Citkowski, P.C.

(57) ABSTRACT

This invention relates to a self-emulsifying solution of Ibuprofen suitable for encapsulation into a soft gelatin capsule.

48 Claims, No Drawings

SELF-EMULSIFYING IBUPROFEN SOLUTION AND SOFT GELATIN CAPSULE FOR USE THEREWITH

FIELD OF THE INVENTION

The present invention generally relates to a pharmaceutical solution. More particularly, the present invention relates to a self-emulsifying solution of ibuprofen suitable for encapsulation into a soft gelatin capsule.

BACKGROUND OF THE INVENTION

It is well known in the art that there are solid drugs which are highly insoluble in water. Due to their low solubilities in water, these drugs have a correspondingly low degree of bioavailability. One such drug, in particular, is ibuprofen. Ibuprofen is a non-steroidal anti-inflammatory drug which is commonly used to relieve pain and to treat inflammatory conditions. Ibuprofen is a white powder or crystal which is practically insoluble in water. Ibuprofen is absorbed from the gastro-intestinal tract and the peak plasma concentrations occur approximately one to two hours after ingestion of the solid powder or crystal form.

A standard dosage form widely in use for the delivery of ibuprofen is the solid dosage form or tablet. The absorption time of a solid dosage form (tablet) is relatively long because of two significant factors. The first factor is that the drug; being introduced as a solid, needs to first dissolve before it can be absorbed by the body. The second factor is that absorption into the body is further delayed because ibuprofen is practically insoluble in water or the acidic environment of the stomach.

Several processes have been developed in efforts to increase the solubility and, hence, the bioavailability of ibuprofen. One such prior art process disclosed in U.S. Pat. No. 5,071,643 to Yu et al., discloses the use of a water-based solvent system for enhancing the solubility of an acidic, basic, or amphoteric pharmaceutical agent, such as ibuprofen, to produce a highly concentrated solution suitable for encapsulation. The solvent system includes polyethylene glycol containing 0.2–1.0 mole equivalents of an ionizing agent per mole equivalent of pharmaceutical agent and 1–20% water. This water-based solvent system provides for a highly concentrated solution capable of encapsulation into a small enough vessel, such as a soft gel capsule, to permit easy swallowing and to provide a pharmaceutically effective dose of a pharmaceutical agent such as ibuprofen.

The method disclosed in the Yu et al. reference solubilizes the pharmaceutical agent (ibuprofen) in a water-based solvent system utilizing a solubility enhancing agent to solubilize the ibuprofen.

It would be advantageous and desirable to have an oil-based ibuprofen solution which is capable of supporting ibuprofen concentrations sufficient for encapsulation in a liquid dosage form.

By combining the oil-based ibuprofen solution with a dosage form such as a filled soft gelatin capsule, optimal advantage can be taken of the potential potency and efficacy of the poorly water-soluble ibuprofen. Also, because the formulation is a true solution, content uniformity of dosage is assured. The present invention provides an improved ibuprofen solution and ibuprofen dosage form for providing the relatively water insoluble ibuprofen with a mechanism for greater dissolution and, hence, greater bioavailability than a solid dosage form which includes all of the aforementioned advantages.

SUMMARY OF THE INVENTION

In accordance with the present invention, there is provided a self-emulsifying ibuprofen formulation including a polyoxyethylene castor oil derivative and ibuprofen which increases the stability, concentration, and bioavailability of the scarcely water soluble ibuprofen.

The present invention further provides an ibuprofen dosage form for increasing the stability, concentration, and bioavailability of the scarcely soluble ibuprofen pharmaceutical including a drug delivery vehicle and a liquid formulation including ibuprofen and a polyoxyethylene castor oil derivative disposed within the drug delivery vehicle.

It is a further objective to produce a highly concentrated solution in order to manufacture as small a capsule as possible to facilitate consumer acceptance.

DETAILED DESCRIPTION OF THE PREFERRED EMBODIMENTS

A self-emulsifying ibuprofen oil-based formulation capable of supporting higher ibuprofen concentrations and having enhanced bioavailability is disclosed. The self-emulsifying ibuprofen formulation generally includes a polyoxyethylene castor oil derivative and ibuprofen.

Polyoxyethylene castor oil derivatives are complex mixtures of various hydrophobic and hydrophilic components. These compounds are non-ionic surfactants which are approved for use in oral, topical, and parenteral pharmaceutical formulations. The polyoxyethylene castor oil derivatives are mainly used as emulsifying and solubilizing agents for the production of aqueous liquid preparations containing oils or hydrophobic substances such as, ibuprofen. Preferred examples of these compounds which are suitable for use in the present invention include Polyoxyl 35 Castor Oil (Peg 35CO) and Polyoxyl 40 Hydrogenated Castor Oil (Peg 40HCO). The amount of the polyoxyethylene castor oil derivatives ranges from approximately 30% to approximately 35% by weight.

For Peg 35CO, the hydrophobic constituents comprise approximately 83% of the total mixture with the main component being glycerolpolyethylene glycol ricinoleate. The hydrophilic component (approximately 17%) consists of polyethylene glycols and glycerol ethoxylates. Peg 35CO has an HLB value of approximately 12–14.

For Peg 40HCO, the hydrophobic component is approximately 75% of the total mixture. The hydrophobic component is comprised mainly of fatty acid esters of glycol polyethylene glycol and fatty esters of polyethylene glycol. The hydrophilic fraction (approximately 25%) consists of polyethylene glycols and glycerol ethoxylates. Peg 40HCO has an approximate BLB value of 14–16.

Ibuprofen is solubilized in the polyoxyethylene castor oil derivatives, preferably Peg 35CO and/or Peg 40HCO to produce a solution which is suitable for encapsulation into a drug delivery vehicle such as a soft gelatin capsule. The resultant solution of ibuprofen in the surfactants produces a solution that is water miscible and self-emulsifying upon addition to water. The amount of the ibuprofen in the formulation ranges from approximately 33% to 38% by weight.

It is possible to dissolve large amounts of ibuprofen in only the polyoxyethylene castor oil derivative surfactants described above at an elevated temperature; however, recrystallization can occur upon cooling of the solution to ambient temperatures. In order to prevent the recrystallization of ibuprofen from the solution upon cooling, solution concentrations at ambient temperatures can be enhanced and stabilized by the addition of complexing agents which are designed to prevent the recrystallization of the drug (ibuprofen). One such class of compounds is soluble polyvinyl pyrrolidone (PVP). PVP is a polymeric compound formulated to specific molecular weights which can range from approximately 2000 to 1,500,000 Daltons. PVP has the capacity or property of forming water-soluble complexes with water insoluble drug substances such as ibuprofen. Typically, higher molecular weight PVP's are used as thickeners while low molecular weight PVP's are typically used as solubilizers or crystallization inhibitors. In the present invention, two particular PVP's are of interest: PVP K-12 (molecular weight approximately 2000–3000 Daltons) and PVP K-17 (molecular weight approximately 7000–11,000 Daltons) which are both suitable recrystallization inhibitors. The amount of PVP utilized in the present invention can range from approximately 15–20% in order to prevent recrystallization. Additionally, in order to aid in dissolution of the PVP in the formulation, water may be utilized as required wherein the minimum required amount is approximately 1–2%. It should be noted, that peculiar to the present invention, that the water content is only approximately 20% of the water content which would be required to dissolve the PVP alone. The balance of the PVP is being dissolved by the system although PVP is not soluble in either Peg 35CO or Peg 40HCO or other excipients alone.

A further unique feature of the present formulation is that the excipients, when combined in the amounts set forth above for the formulation, do not form a homogenous solution. That is, the drug, ibuprofen, is an essential part of the formulation in that a solution can not be produced with the above described excipients alone in their prescribed amounts without the addition of ibuprofen. It is the property of ibuprofen to form eutectic solutions with certain compounds, such as the excipients described above, which is novel to the ibuprofen formulation of the present invention. The present invention takes advantage of this property to form a stable solution suitable for encapsulation which can only be produced when all of the ingredients are combined in their prescribed amount and by following a specific formulation procedure.

The ibuprofen formulation is prepared by combining the selected surfactant, such as Peg 35CO or Peg 40HCO with castor oil. The mixture is then stirred and heated to approximately between 50° C. and 70° C., preferably about 60° C. to facilitate the mixing and dissolution of the ibuprofen. Then, the described amount of ibuprofen, the selected PVP, and water are added to the selected surfactant. The mixture is stirred continuously until a true solution is formed. The solution is then cooled to room temperature.

In addition to the ingredients described above, in order to provide an ibuprofen solution formulation that is suitable for encapsulation into a drug delivery vehicle, preferably a soft gelatin capsule, the viscosity of the ibuprofen formulation may be adjusted in order to produce adequate flow characteristics. In such cases, the viscosity of the ibuprofen formulation can be adjusted with an oil compatible with the polyoxyethylene castor oil derivatives described above. One such compatible oil is castor oil which may be added to the formulation in amounts ranging from approximately 7%–15%.

The ibuprofen dosage form according to the present invention includes a drug delivery vehicle and the self-emulsifying ibuprofen formulation disposed within the drug delivery vehicle. The drug delivery vehicle can be a two-piece, standard gelatin capsule which typically includes a first capsule half and a second capsule half which is well known to those of ordinary skill in the art. More preferably, the drug delivery vehicle is a soft gelatin capsule which is a one-piece, hermetically sealed gelatin based capsule which can be made by techniques known to those skilled in the art. As immediately stated above, the soft gelatin capsule is preferred to the conventional two-piece type capsule as the soft gelatin capsule does not require any additional sealing of the capsule halves as would be required with the liquid filled two-piece type capsule, and commensurately, is less prone to deliberate tampering or contamination.

In developing the soft gelatin capsule ibuprofen dosage form according to the present invention, it must be recognized that the capsule is a system comprised of the ibuprofen formulation and the gelatin shell used to encapsulate the ibuprofen formulation. As such, not only is the filled ibuprofen formulation critical to produce the desired bioavailability characteristics but the gelatin formulation is also critical as it must be compatible with the ibuprofen formulation. One skilled in the art would be aware of the potential fill-shell interactions which could result in both physical and chemical capsule instability. Accordingly, the gelatin formulation utilized to form the capsule for the ibuprofen dosage form is also critical to the present invention.

In general, gelatin capsule formulations for soft gelatin capsules consist of raw gelatin and one or more ingredients which are added to plasticize the gelatin to produce a capsule to suitable hardness as required by design or by preference. Typical plasticizers include glycerin and sorbitol. Also, sorbitan anhydrides and mannitol may also be utilized. Furthermore, other non-traditional ingredients may be used to plasticize the gelatin such as polyethylene glycol 200 (PEG 200).

In the present invention, applicants determined that glycerin could react with the ibuprofen to form unwanted glycerol esters of ibuprofen and generate a fill/shell interaction as described above. As such, the gelatin formulations suitable for use with the ibuprofen formulation of the present invention provide the necessary physical and chemical stability required for use with the ibuprofen formulation of the present invention.

The preferred gelatin formulation for use in constructing soft gelatin capsules for use with the ibuprofen formulation of the present invention includes gelatin in the range of approximately 40% to approximately 48% and a plasticizer ranging in amount from approximately 20% to approximately 35%. Suitable plasticizers for use with the preferred capsule formulation include sorbitol USP, a non-crystallizing sorbitol solution, and PEG 200. When sorbitol alone is utilized as the plasticizer, the amount can range from approximately 25% to approximately 30%. A more preferred plasticizer is a non-crystallizing sorbitol solution of composition of approximately 40% to approximately 50% sorbitol, approximately 15% to approximately 25% 1,4-sorbitan, and approximately 1% to approximately 10% mannitol, all percentages are by weight.

The capsule formulations can also include other suitable additives such as preservatives and/or coloring agents which are utilized to stabilize the capsule and/or impart a specific characteristic such as color or look to the capsule. Pharmaceutically acceptable preservatives can include, for example, methyl and propyl parabens. Color may be imparted to the gelatin shell using FD&C and/or D&C dyes. Opacifiers, such as titanium dioxide and/or iron oxides, may be employed to color and/or render the capsule opaque.

Below are examples illustrating several soft gelatin capsule formulations along with several examples of ibuprofen formulations made in accordance with the present invention. The examples presented below are intended to illustrate particular embodiments of the invention and are not intended to limit the scope of the specification, including the claims, in any way.

EXAMPLES

Gelatin Formulations—Soft Gel Formulations

Example 1

| | |
|---|---|
| Gelatin | 41.5% |
| Sorbitol Solution | 30.0% |
| Water | 28.5% |

Example 2

| | |
|---|---|
| Gelatin | 43.5% |
| Sorbitol Solution | 26.0% |
| Water | 30.5% |

Example 3

| | |
|---|---|
| Gelatin | 45.5% |
| Sorbitol Solution | 27.2% |
| Water | 27.3% |

Example 4

| | |
|---|---|
| Gelatin | 47.0% |
| PEG 200 | 15.0% |
| Sorbitol Solution | 6.0% |
| Water | 32.0% |

Example 5

| | |
|---|---|
| Gelatin | 47.5% |
| PEG 200 | 20.0% |
| Water | 32.5% |

Ibuprofen Fill Formulations

Example 6

| | |
|---|---|
| Ibuprofen | 200 Mg. |
| PVP K-12 | 100 Mg. |
| Water | 10 Mg. |
| Peg 35 CO | 200 Mg. |
| Castor Oil | 90 Mg. |
| Fill Wt. | 600 Mg. |

Example 7

| | |
|---|---|
| Ibuprofen | 200 Mg. |
| PVP K-17 | 100 Mg. |
| Water | 10 Mg. |
| Peg 35 CO | 200 Mg. |
| Castor Oil | 90 Mg. |
| Fill Wt. | 600 Mg. |

Example 8

| | |
|---|---|
| Ibuprofen | 200 Mg. |
| PVP K-17 | 100 Mg. |
| Water | 10 Mg. |
| Peg 40 HCO | 200 Mg. |
| Castor Oil | 90 Mg. |
| Fill Wt. | 600 Mg. |

Example 9

| | |
|---|---|
| Ibuprofen | 200 Mg. |
| PVP K-12 | 100 Mg. |
| Water | 10 Mg. |
| Peg 40 CHO | 200 Mg. |
| Castor Oil | 90 Mg. |
| Fill Wt. | 600 Mg. |

Example 10

Dissolution Profile of the Ibuprofen Capsule

The dissolution profile of the formulation described in Example 6, which was encapsulated into a 9.5 minim oblong soft gelatin capsule, was determined using the USP dissolution apparatus #2.

The paddles were set at 100 RPM and the dissolution medium was 37° C. water.

The release of the drug was determined by HPLC using a UV detector at 220 nm.

The dissolution results are presented in the table below.

| TIME | % IBUPROFEN |
|---|---|
| 15 Minutes | 95.6% |
| 30 Minutes | 100.0% |
| 45 Minutes | 99.9% |
| 60 Minutes | 101.5% |

In view of the teachings presented herein, other modifications and variations of the present inventions will be readily apparent to those of skill in the art. The foregoing discussion and description are illustrative of some embodiments of the present invention, but are not meant to be limitations on the practice thereof. It is the following claims, including all equivalents, which define the scope of the invention.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

What is claimed:

1. A clear ibuprofen solution, said solution consisting essentially of:
   a polyoxyethylene derivative of castor oil;
   polyvinylpyrrolidone; and
   ibuprofen.

2. A formulation according to claim 1, comprising castor oil.

3. A formulation according to claim 1, comprising water.

4. A formulation according to claim 1, wherein the amount of said polyoxyethylene castor oil derivative ranges from approximately 30% to approximately 35% by weight.

5. A formulation according to claim 1, wherein the amount of said ibuprofen ranges from approximately 33% to approximately 38% by weight.

6. A formulation according to claim 2, wherein the amount of castor oil ranges from approximately 7% to approximately 15% by weight.

7. A formulation according to claim 1, wherein the amount of polyvinylpryyolidone ranges from approximately 15% to approximately 20% by weight.

8. A formulation according to claim 3, wherein the amount of water ranges from approximately 1% to approximately 2% by weight.

9. A formulation according to claim 1, wherein said polyoxyethylene castor oil derivative comprises polyoxyl 35 castor oil.

10. A formulation according to claim 1, wherein said polyoxyethylene castor oil derivative comprises polyoxyl 40 hydrogenated castor oil.

11. A formulation according to claim 1, wherein said polyoxyethylene castor oil derivative has an HLB value ranging between approximately 12 and approximately 16.

12. A formulation according to claim 1, wherein said polyvinylpyrrolidone has a molecular weight ranging from approximately 2,000 to 11,000 Daltons.

13. An ibuprofen dosage form, said dosage form comprising:
   a drug delivery device; and
   a liquid solution consisting essentially of ibuprofen; polyvinylpyrrolidone; and a polyoxyethylene derivative of castor oil disposed within said drug delivery device.

14. A dosage form according to claim 13, comprising castor oil.

15. A dosage form according to claim 13, comprising water.

16. A dosage form according to claim 13, wherein the amount of said polyoxyethylene castor oil derivative range from approximately 30% to approximately 35% by weight.

17. A dosage form according to claim 13, wherein the amount of said ibuprofen ranges from approximately 33% to approximately 38% by weight.

18. A dosage form according to claim 14, wherein the amount of castor oil ranges from approximately 7% to approximately 15% by weight.

19. A dosage form according to claim 13, wherein the amount of polyvinylpryyolidone ranges from approximately 15% to approximately 20% by weight.

20. A dosage form according to claim 15, wherein the amount of water ranges from approximately 1% to approximatey 2% by weight.

21. A dosage form according to claim 15, wherein said polyoxyethylene castor oil derivative comprises polyoxyl 35 castor oil.

22. A dosage form according to claim 15, wherein said polyoxyethylene castor oil derivative comprises polyoxyl 40 hydrogenated castor oil.

23. A dosage form according to claim 15, wherein said polyoxyethylene castor oil derivative has an HLB value ranging between approximately 12 and approximately 16.

24. A dosage form according to claim 13, wherein said polyvinylpyrrolidone has a molecular weight ranging from approximately 2,000 to 11,000 Daltons.

25. A dosage form according to claim 13, wherein said drug delivery device comprises a capsule.

26. A dosage form according to claim 25, wherein said capsule comprises a soft gelatin capsule.

27. A dosage form according to claim 25, wherein said capsule is substantially comprised of gelatin.

28. A dosage form according to claim 25, wherein said capsule comprises a first capsule half and a second capsule half.

29. A dosage form according to claim 25, wherein said capsule further comprises an opacifying agent.

30. A dosage form according to claim 29, wherein said opacifying agent comprises titanium dioxide or iron oxide.

31. A dosage form according to claim 25, wherein said capsule further comprises a preservative agent.

32. A dosage form according to claim 31, wherein said preservative agent comprises methyl- or propyl-parabens.

33. A dosage form according to claim 25, wherein said capsule comprise a plasticizer.

34. A dosage form according to claim 33, wherein said plasticizer comprises sorbitol.

35. A dosage form according to claim 33, wherein said plasticizer comprises non-crystallizing sorbitol solution.

36. A dosage form according to claim 35, wherein said plasticizer comprises a sorbitan.

37. A dosage form according to claim 35, wherein said plasticizer comprises mannitol.

38. A dosage form according to claim 35, wherein said plasticizer comprises a mixture of sorbitol, sorbitan, and mannitol.

39. A method of making an ibuprofen dosage form, said method comprising the steps of:
   mixing ingredients consisting essentially of a polyoxyethylene derivative of castor oil, ibuprofen and polyvinylpyrrolidone to form a solution; and
   disposing the solution of the polyoxyethylene derivative of castor oil, polyvinylpyrrolidone, and ibuprofen into a drug delivery device.

40. A method according to claim 39, wherein the drug delivery device comprises a capsule.

41. A method according to claim 40, wherein the drug delivery device comprises a two-piece capsule.

42. A method according to claim 40, wherein the capsule comprises a soft gelatin capsule.

43. A method according to claim 39, wherein said mixing step further comprises castor oil.

44. A method according to claim 39, wherein said mixing step further comprises water.

45. A method according to claim 39, further comprising the step of heating the polyoxyethylene castor oil derivative to a temperature ranging from 50° C. to approximately 70° C. prior to the addition of the ibuprofen.

46. A clear ibuprofen solution, said solution consisting essentially of:

a polyoxyethylene derivative of castor oil;
polyvinylpyrrolidone;
ibuprofen; and
polyethylene glycol present in an amount less than 6% by weight.

47. An ibuprofen dosage form, said dosage form comprising:
   a drug delivery device; and
   a liquid solution consisting essentially of ibuprofen; polyvinylpyrrolidone; a polyoxyethylene derivative of castor oil, and polyethylene glycol in an amount less than approximately 6% by weight disposed within said drug delivery device.

48. A method of making an ibuprofen dosage form, said method comprising the steps of:
   mixing ingredients consisting essentially of a polyoxyethylene derivative of castor oil, ibuprofen, polyvinylpyrrolidone, and polyethylene glycol in an amount less than approximately 6% by weight, to form a clear solution; and
   disposing the solution of the polyoxyethylene derivative of castor oil, polyvinylpyrrolidone, ibuprofen, and polyethylene glycol into a drug delivery device.

* * * * *